United States Patent [19]

Wieland et al.

[11] Patent Number: 4,584,187

[45] Date of Patent: Apr. 22, 1986

[54] IMAGING AGENT AND METHOD OF USE

[76] Inventors: Donald M. Wieland, 1204 Linwood, Ann Arbor, Mich. 48103; Lawrence E. Brown, 523 Thomas St., Ypsilanti, Mich. 48197; William H. Beierwaltes, 1025 Forest Rd., Ann Arbor, Mich. 48105; Jiann-long Wu, 2672 Velvet Way, Walnut Creek, Calif. 94596

[21] Appl. No.: 250,059

[22] Filed: Apr. 1, 1981

[51] Int. Cl.[4] .................. A61K 43/00; A61K 49/00
[52] U.S. Cl. ........................................ 424/1.1; 424/9; 564/238
[58] Field of Search .................. 424/1, 9; 564/238

[56] References Cited

U.S. PATENT DOCUMENTS

| | | | |
|---|---|---|---|
| 4,022,877 | 5/1977 | Huber et al. | 424/1 |
| 4,083,947 | 4/1978 | Monks et al. | 424/1 |
| 4,215,045 | 7/1980 | Knapp, Jr. | 424/1 |

OTHER PUBLICATIONS

Wieland et al., Chem. Abstracts, vol. 93 (1980) #21668j; abstracting Wieland et al., J. Nucl. Med., 1980, 21(4), 349–353.

Swanson et al., Chem. Abstracts, vol. 95 (1981) #164728f.

Wieland et al., J. Nucl. Med., 1981, 22(4), 358–364.

Primary Examiner—Christine M. Nucker
Attorney, Agent, or Firm—Harness, Dickey & Pierce

[57] ABSTRACT

A new radiopharmaceutical composition for use in nuclear medicine comprises a radioiodinated meta-iodobenzylguanidine. The composition is used as an imaging agent for the heart, adrenal medulla, and tumors of the adrenal medulla and can be used for treatment of tumors of the adrenal medulla.

21 Claims, No Drawings

IMAGING AGENT AND METHOD OF USE

The government has rights in this invention pursuant to Contract No. DE-AC02-76EV02031 awarded by the U.S. Department of Energy.

BACKGROUND OF THE INVENTION

The present invention relates to radiolabeled compounds and their method of use in clinical nuclear medicine. More specifically, the present invention relates to radioiodinated meta-iodobenzylguanidine and its method of use as an imaging agent, particularly for the heart, adrenal medulla, and tumors of the adrenal medulla. In addition, the present invention relates to the method of use of radioiodinated meta-iodobenzylguanidine as a treatment agent for tumors of the adrenal medulla.

Radiolabeled compounds which are subject to localization in particular organs or tumors therein are of great value for diagnosis and/or therapeutic purposes for diseases of the human body. For example, Thallium-201 and fatty acids labeled with carbon-11 and iodine-123 have been utilized as heart imaging agents. Also, various phosphonate ligands labeled with technetium-99m have been used to image infarcted regions of the heart. However, although many useful radiolabeled compounds are known, there remains a need for the discovery of additional or improved compounds which are effective for routine imaging of particular organs, tissues, or tumors therein. In addition, there remains an obviious need for radiolabeled compounds which are useful in treating tumors of specific organs of the human body.

Although the agent I-131-6B-idodomethyl-19-norcholest-5-(10)-en-3B-ol has been and is being used for imaging the adrenal cortex and its tumors, before the present invention no radiolabeled compound was known which could routinely image the adrenal medulla or tumors of the adrenal medulla. The adrenal medulla, although anatomically contiguous with the adrenal cortex, is an entirely separate tissue both embryologically and functionally. Hence, the need for an agent effective to image the adrenal medulla is readily apparent.

There is also a need for an improved imaging agent for the heart. Although thallium-201 is used for heart imaging, it is expensive and has less than optimum nuclear imaging properties. Carbon-11 fatty acids can be used for heart imaging but their use is severely limited by the requirement for an in-house cyclotron for the product of the short-lived isotope (Tl/2=20 min) C-11. The use of iodine-123 fatty acids is still being evaluated in various nuclear medicine clinics throughout the world, but these compounds have a short biologic Tl/2 (about 10 minutes) in the heart. Technetium-99m labeled diphosphonates are useful heart imaging agents but are not heart perfusion agents and are limited to imaging only severely damaged or infarcted regions of the heart.

Accordingly, the present invention provides a novel radiopharmeceutical compound, radioiodinated metaiodobenzylguanidine, and its method of use as an exceptional imaging agent, particularly for the adrenal medulla, tumors of the adrenal medulla and the heart. A method of using radioiodinated meta-iodobenzylguanidine as a therapeutic agent for the treatment of tumors, particularly tumors of the adrenal medulla, is also provided by the present invention.

SUMMARY OF THE INVENTION

The present invention relates to a novel radiopharmaceutical compound, radioiodinated metaiodobenzylguanidine, and its method of use as a diagnostic and therapeutic agent. A radiopharmaceutical composition of the present invention comprises radioiodinated metaiodobenzylguanidine and a pharmeceutical carrier such as a physiological buffered saline solution. A method for treating tumors of the adrenal medulla comprises the step of systemically applying to a human a radiopharmaceutical composition comprising radioiodinated meta-iodobenzylguanidine. A method for diagnostic imaging comprises the steps of systemically applying to a human radiopharmeceutical composition comprising radioiodinated meta-iodobenzylguanidine and subsequently making an image by detecting gamma radiation emitted by said radiological composition following its localization in the target organ.

DESCRIPTION OF THE INVENTION

Despite the physiological importance of norepinephrine as an adrenergic transmitter, no radiopharmaceutical heretofore existed for assessing catecholamine hormone accumulation and turnover in peripheral tissue. Meta-iodobenzylguanidine is an iodinated analog of guanethidine, an adrenergic neuronal blocking agent. It has now been discovered that meta-iodobenzylguanidine is accumulated in adrenergic tissues in a manner similar to norepinephrine and guanethidine and therefore localizes in the adrenergic neurons of the heart and chromaffin granules of the adrenal medulla. Accordingly, it has been discovered that radioiodinated meta-iodobenzylguanidine is a useful radiopharmaceutical for imaging the heart, adrenal medulla, and tumors of the adrenal medulla.

Radioiodinated meta-iodobenzylguanidine compounds suitable for use herein can be synthesized as illustrated in Examples I-III. The I-123 radiolabel is preferably employed as an imaging agent for the heart while the I-131 radiolabel, which has a longer half-life, is preferably employed as an imaging agent for the adrenal medulla, and, of course, as a therapeutic agent.

A pharmaceutical composition of the present invention comprises one of the aforementioned isotopes of radioiodinated meta-iodobenzylguanidine and a carrier such as a physiological buffered saline solution. It is contemplated that the composition will be systematically administered to the patient as by intravenous injection. Suitable dosages for use as a diagnositc imaging agent are from about 0.2 to about 1.0 mCi of I-131 labeled meta-iodobenzylguanidine for the adrenal medulla or tumors therein, and from about 1.0 to about 3.0 mCi of the I-123 labeled agent for imaging of the heart. For use as a theapeutic agent, a higher dosage is required, for example, from about 100 to about 200 mCi of the I-131 labeled material.

It will be appreciated by those skilled in the art that the novel imaging agent of the present invention is employed in accordance with conventional methdology in nuclear medicine. Thus, a composition of the present invention is systemically applied to the patient and subsequently the uptake of the composition in the selected organ is measured and an image formed, for example, by means of a conventional gamma camera.

Further understanding of the present invention can be obtained from the following examples and from Kline et al.: "Myocardial imaging in man with [$^{123}$I]-metaiodobenzylguanidine," *J.Nucl.Med.* 22:129-132, 1981; Wieland et al: "Myocardial imaging with a radioiodinated norepinephrine storage analog," *J. Nucl. Med.* 22:22-31, 1981; Valk et al: "Evolution of pheochromocytoma in multiple endocrine neoplasia: A scintigraphic portrayal using $^{131}$I-metaiodobenzylguanidine," *Ann. Int.Med.*, 94: June 1981; and Sisson, et al: "Scintigraphic localization of pheochromocytoma," submitted to *New Eng. J. Med.*, March 1981; all of these articles are specifically incorporated be reference herein.

EXAMPLE I $I^{131}$-meta-iodobenzylguanidine was synthesized in accordance with the following procedure.

Part A. Meta-iodobenzylguanidine Sulfate

A mixture of m-iodobenzylamine hydrochloride (539 mg, 2.0 mmol) (from Phaltz and Bauer, Inc., of Stamford, Conn.) and cynanmide (127 mg, 3.0 mmol) was stirred and heated in an oil bath at 100° C. for 4 hours. The resulting glassy solid dissolved in 1 ml of $H_2O$ and a solution of $KHCO_3$ (200 mg, 2.0 mmol) in 1 ml of water was added dropwise with stirring. The precipitated m-iodobenzylguanidine bicarbonate was then collected, washed with cold water and dried in vacuo: yield 575 mg (85%), mp 124°-126° C.

To the m-iodobenzylguanidine bicarbonate (539 mg, 1.6 mmol) in 5 ml of water was slowly added 0.8 ml (1.6 mEq) of $2N$ $H_2SO_4$. The resulting suspension was warmed to solution and the desired guanidine sulfate crystallized on cooling to room temperature. The colorless crystals were collected, washed with cold water and dried in vacuo: yield 403 mg (78%), mp 164°-167° C. Recrystallization from $H_2O$-EtOH provided m-iodobenzylguanidine sulfate as colorless crystals: mp 166°-167° C.; HPLC [THF/0.1M $NaH_2PO_4$ 12/88, 3.0 ml/min] showed only one peak $t_R=8.6$ min; IR (nujol) 3340 (NH), 3160 (NH), 1660 and 1630 (C=N), 1090 (S=O), 780 and 695 cm (1,3-disubstituted benzene); PMR ($CD_3OD$) δ4.36 (S,2,$CH_2$), 6.96-7.73 [m(7 peaks), 4,arom]; the aromatic peak pattern was identical to that observed for m-iodobenzylamine hydrochloride in $CD_3OD$. Anal. Calcd for $C_8H_{10}IN_3$ .$O.5H_2SO_4$: C,29.64; H, 3.42. Found C,29.55,H, 3.40.

Part B. $I^{131}$-meta-iodobenzylguanidine

Dissolve 0.2-4.0 mg of meta-iodobenzylguanidine sulfate (from Part A) in 0.6 ml of deionized and redistilled water in a 10 ml round bottom reaction flask fitted with an air condenser and a micro-sized Teflon ® stirring bar. Evaporate off the water. Add 0.4 ml of 0.1M Ammonium Dihydrogen Phosphate buffer and 10 mCi of $^{131}$I-Sodium Iodide (carrier-free) to the reaction flask. The solution was heated to reflux temperature (oil bath at 140° C.) for 20-30 minutes during which time the water slowly evaporated away. More water (0.20-0).40 ml) was added while maintaining the same oil bath temperature. The water again was allowed to evaporated and the procedure was repeated continuously for a total reaction time 3 hours. The solution was cooled to room temperature and the residue dissolved in 1.0 ml of water and passed through a glass column packed with 1.5 g of Cellex D anion exchange cellulose (Bio Rad of Richmond, Calif.) equilibrated with 0.005M Acetate Buffer to remove unreacted iodide and any iodate that was formed. Elute the $^{131}$I-metaiodobenzylguanidine buffer from the column using 6.0 ml of 0.005M Acetate Buffer. The final volume is made to 10 ml using Bacteriostutic Normal Saline Solution, U.S.P. The radiochemical yield was 90-95% resulting in a specific activity range of 2-40 mCi/mg.

The radiochemical purity was greater than 98% as determined by thin-layer chromotography on silica gel G using two solvent systems: (1) 1/1 ethyl acetate: ethanol (Rf=0.0; Rf of free radioiodide=0.60); (2) 3/1 n-propanol: 10% ammonium hydroxide (Rf=0.15, Rf of free radioiodide=0.75, Rf of meta-iodobenzylamine=0.35). The radiolabeled compound showed no detectable decomposition for up to 4 days when stored as the sulfate salt in water or physiological saline at 4° C. in the dark. Final pH≈6.0.

Since the Rf's of the three isomeric guanidines are nearly identical in the above TLC systems, radio-HPLC was needed to verify the absence of rearranged isomeric impurities. The radiochemical purity of I-125-paraiodobenzylguanidine was routinely found to be > 98% on a μBondapak C18 column (THF/0.1M $NaH_2PO_4$12/88, 2.0 ml/min). With this HPLC system, the retention times ($t_R$) of the meta, para and ortho isomers were 12'20", 15'20", and 6'40" respectively. The absence of I-125-2,4-diiodobenzylguanidine ($t_R=32'25"$ at 3.0 ml/min), a potential impurity that could arise from electrophilic addition to the aromatic ring, was also verified.

EXAMPLE II $I^{123}$-meta-iodobenzylguanidine was synthesized in accordance with the following procedure.

First, meta-iodobenzylguanidine sulfate was made as in Example I, Part A. Then, to a 10 ml round bottom flask containing 0.20-4.0 mg of meta-iodobenzylguanidine sulfate was added 0.4 ml of 0.1M $NH_4H_2PO_4$ solution followed by approximately 20 mCi of NaI-123 in 0.10-1.0ml of 0.1M NaOH (from Crocker Nuclear Laboratories of Davis, Calif.).

The reaction was then carried out as in Part B of Example I. Radiochemical yields are nearly as high as obtained for the I-131 exchange method of Example I and the purity determination was the same as reported in Example I. The I-123-labeled compound shows minimal detectable radio-composition for up to 4 days when dissolved as the sulfate salt in water or physiological buffered saline at 4° C. in the dark.

EXAMPLE III

The procedures of Example I are carried out except that meta-iodobenzylguanidine of Part A is synthesized by the following route: a solution of m-iodobenzylamine (500 mg 2.0 mmol) and 2-methyl-2-thiopseudourea sulfate (278 mg, 1.0 mmol) in 10 ml of 50% ethanol was heated at reflux for 4 hours. Upon cooling to 4° C. for 24 hours, the crystalline precipitate was vacuum filtered and recrystallized from $H_2O$-EtoH to give 200 mg (40% yield) of product, mp 163°-165° C.

EXAMPLE IV

The procedures of Example I were carried out except that Part B was carried out as follows. 0.2-2.0 mg of meta-iodobenzylguanidine sulfate, 5-20 mCi of NaI-125 and 2-4 mg of ammonium sulfate were dissolved in deionized and redistilled water solvent. The solvent was removed by heating and the mixture heated at 120°-160° C. (below the melting point of the substrate) for 1-4 hours. The reaction mixture was then dissovled in water and unreacted iodide and iodate were removed by anion exchange chromatography on a Cellex-D (Biorad) column eluted with 5 mM, pH4 acetate buffer. The radiochemical yield was greater than 95%.

EXAMPLE V

Biological tissue distribution studies were performed on rats, dogs and monkeys injected intravenously with 25 µCi and 100 µCi respectively of I-125 iodobenzylguanidine in an average volume of 0.3 ml, 2 ml, and 1 ml respectively. Representative samples of tissues were counted in an autogamma counter with corrections made for radioactive decay, background, and counter efficiency. To normalize for differences in animal weights, tissue concentrations are expressed as percent kilogram dose per gram. The results are set forth below:

| A. Rats (6) at 30 min. | |
| --- | --- |
| Tissue | % Kg Dose/g (Mean ± S.E.M.) |
| Heart | 1.09 ± .06 |
| Blood | .03 ± .00 |
| Liver | .36 ± .02 |
| Lung | .70 ± .06 |
| Muscle | .25 ± .02 |
| Thyroid | .76 ± .04 |

| B. Female Mongrel Dogs (2): | | | |
| --- | --- | --- | --- |
| | % Kg Dose/g (Mean ± S.E.M.) | | |
| Tissue | 30 min. | 2 hours | 48 hours |
| Adrenal Medulla | 5.35 ± .71 | 6.29 ± .25 | 13.6 ± 1.1 |
| Adrenal Cortex | 0.61 ± .02 | 0.39 ± .05 | 0.10 ± .01 |
| Heart | 0.47 ± .02 | 0.50 ± .10 | 0.06 ± .01 |
| Blood | 0.02 ± .00 | 0.02 ± .00 | 0.01 ± .00 |
| Liver | 0.34 ± .03 | .017 ± .05 | 0.02 ± .00 |
| Lung | 0.22 ± .06 | 0.46 ± .13 | 0.03 ± .00 |
| Muscle | 0.02 ± .00 | 0.04 ± .00 | 0.02 ± .00 |
| Thyroid | 0.56 ± .07 | 0.56 ± .05 | 1.27 ± .47 |

| C. Rhesus Monkeys (3) at 3 hours | |
| --- | --- |
| Tissue | % Kg Dose/g (Mean ± S.E.M.) |
| Adrenal Medullae | 2.69 ± .28 |
| Adrenal Cortex | 0.42 ± .12 |
| Heart | 0.64 ± .03 |
| Blood | 0.02 ± .00 |
| Liver | 0.76 ± .03 |
| Lung | 0.17 ± .00 |
| Muscle | 0.02 ± .00 |

EXAMPLE VI

Pheochromocytomas (PHEO) were localized with I-131-meta-iodobenzylguanidine ($^{131}$I-mIBG). Five hypertensive patients without PHEO served as controls. I-131-mIBG, 0.5 mCi, was given i.v. Images of areas of interest were made at 24, 48 and 72 hours post-injection. Adrenal (tumor) uptake was estimated with a semioperator-independent computer algorithm. All patients with sporadic PHEO gave clinical and hormonal evidence of their disease.

Control subjects exhibited little or no scintigraphic image of their adrenal glands. The eight patients studied exhibited a broad spectrum of PHEOs: intra-and extraadrenal tumors; benign and malignant disease; tumor masses of 0.43 to 63 gms; and tumors which secreted both norepinephrine and epinephrine as well as those that produced predominantly norepinephrine. In each of the eight patients, scintigrams made with $^{131}$I-mIBG located abnormal collections of activity. These abnormalities correspond to PHEOs that were subsequently excised in 7 of the 8 patients. The layer intra-adrenal tumors were readily detected by computerized tomography (CAT-Radiology studies ), but in 4 of these patients the CAT technique failed to localie the PHEO. In patients with malignant (metastatic) PHEOs, multiple areas of activity were seen in the skull, chest and abdomen of one; in another, only ill-defined activity was seen. Calculated % uptake ranged from 0,14 to 2.6%/dose.

EXAMPLE VII

To display adrenal medullary abnormalities, 500 µCi of $^{131}$I-mIBG was injected into 6 patients from 5 families with MEN-2 and scintiscans were performed 1 and 2 days later. Percent administered dose uptake was calculated using a semioperator independent algorithm. Adrenal medullary function was assessed by plasma norepinephrine (N) and epinephrine (E) and urinary N, E, metanephrine (M), and normetanephrine (NM) levels.

| Patient | Plasma+ | Urine+ | MIBG Adrenal Imaging |
| --- | --- | --- | --- |
| 1* | Normal | Normal | Nonvisualized |
| 2 | Normal | Normal | Nonvisualized |
| 3 | Normal | ↑M | Faint bilateral |
| 4** | ↑N | ↑NM | Distinct bilateral |
| 5 | ↑N,E | ↑E,NM,M | Distinct bilateral |
| 6 | ↑N,E | ↑E,NM,M | Asymmetric bilateral |

*apparently unaffected;
**MEN 2b (others MEN 2a);
+abnormal are greater than 3 SD above normal mean.

Patient 1 was at 50% risk for MEN 2a but was apparently unaffected as he had normal calcitonin levels as well as medullary hormones. Neither patient 1 nor patient 2, who was affected with medullary thyroid carcinoma, showed adrenal imaging with $^{131}$I-mIBG, a pattern recognized by control studies as normal. In the remaining 4 patients, the percent uptakes of $^{131}$I-mIBG by the adrenal glands increased proportionally to the urine and plasma hormone values. Patient 6 has asymmetric bilateral pheochromocytomas. The right adrenal gland showed two distinct tumors with $^{131}$I-mIBG scintigraphy which were confirmed at surgery but which were shown only as an irregular area on CT.

$^{131}$I-mIBG scintigraphy is a new approach in the localiztion of adrenal medulla abnormalities in MEN 2. These scintigrams portray a combination of functional and anatomic changes that chart the evoultion of pheochromocytoma in people affected with MEN 2 syndrome.

EXAMPLE VIII

I-123-meta-iodobenzylguanidine ($^{123}$I-m-IBG), was used to image the myocardium in 5 normal male volunteers. Each subject received 2.0 mCi $^{123}$I-m-IBG intravenously. Four were given a bolus injection. Cardiac imaging was performed in a 40° left anterior oblique projection using a standard field of view gamma camera equipped with a low energy high sensitivity collimator. A 25% window was used, centered at 159 KeV gamma of I-123. A 60 second dynamic acquisition at one frame/second was begun simultaneously with the $^{123}$I-m-IBG injection. Five minute images were acquired sequentially for 60 minutes and again at 90 and 120 minutes. Additional 50,000 count images were obtained on a wide field of view gamma camera with pinhole collimation. Myocardial percent uptake was calculated by dividing the decay corrected global myocardial count rate following interpolated background correction by the peak count rate obtained during the first passage of the $^{123}$I-m-IBG bolus through the heart.

All data were recorded onto a dedicated Nuclear Medicine minicomputer for display, videoformatting, and quantitative analysis.

It will be readily apparent that one skilled in the art having benefit of the foregoing disclosure of the present invention may make modifications or variations of the invention without departing from the spirit thereof. Therefore, it is intended that the scope of the present invention be limited by the spirit and content of the appended claims.

What is claimed is:

1. A radioiodinated compound I-metaiodobenzylguanidine wherein I is an isotope selected from $I^{123}$ and $I^{131}$.

2. The compound of claim 1 wherein I is the 123 isotope.

3. The compound of claim 1 wherein I is the 131 isotope.

4. A radiopharmeceutical comprising radioiodinated I-meta-iodobenzylguanidine and a carrier.

5. The composition of claim 4 wherein said carrier is a physiological buffered saline solution.

6. The composition of claim 4 comprising $^{123}I$-meta-iodobenzylguanidine.

7. The composition of claim 4 comprising $^{131}I$-meta-iodobenzylguanidine.

8. The composition of claim 6 wherein said $^{123}I$-meta-iodobenzylguanidine is present in an effective amount of from about 1.0 to about 3.0 mCi.

9. The composition of claim 7 wherein said $^{131}I$-meta-iodobenzylguanidine is present in an effective amount of from about 0.2 to about 1.0 mCi.

10. The composition of claim 7 wherein said $^{131}I$-meta-iodobenzylguanidine is present in an effective amount of from about 100 to about 200 mCi.

11. A method of radio-imaging a human organ comprising the steps of:
    (a) systemically applying a pharmaceutical composition comprising radioiodinated meta-iodobenzylguanidine to a human;
    (b) detecting gamma radiation emitted by said composition and forming an image therefrom.

12. The method of claim 11 wherein said pharmaceutical composition comprises a physiological buffered saline carrier.

13. The method of claim 11 wherein said composition comprises $^{123}I$-meta-iodobenzylguanidine.

14. The method of claim 13 wherein said $^{123}I$-meta-iodobenzylguanidine is present in an effective amount of from about 1.0 to about 3.0 mCi.

15. The method of claim 11 wherein said composition comprises $^{131}I$-meta-iodobenzylguanidine.

16. The method of claim 15 wherein said $^{131}I$-meta-iodobenzylguanidine is present in an effective amount of from about 0.2 to about 1.0 mCi.

17. The method of claim 11 wherein said human organ is selected from the group consisting of the heart, adrenal medulla, and tumors of the adrenal medulla.

18. A method of therapeutically treating a tumor, comprising systemically applying a pharmaceutical composition comprising radioiodinated meta-iodobenzylguanidine to a human.

19. The method of claim 18 wherein said composition comprises, in addition, a physiological buffered saline carrier.

20. The method of claim 18 wherein said composition comprises $^{131}I$-meta-iodobenzylguanidine.

21. The method of claim 20 wherein said $^{131}I$-meta-iodobenzylguanidine is present in an effective amount of from about 100 to about 250 mCi.

* * * * *